US006826578B2

(12) United States Patent
Brackett et al.

(10) Patent No.: US 6,826,578 B2
(45) Date of Patent: Nov. 30, 2004

(54) METHOD, SYSTEM, AND COMPUTER PRODUCT FOR COLLECTING AND DISTRIBUTING CLINICAL DATA FOR DATA MINING

(75) Inventors: Cameron Brackett, Naperville, IL (US); Virinchipuram Jagannathan Anand, Brookfield, WI (US)

(73) Assignee: GE Medical Systems Information Technolgoies, Inc., Milwaukee, WI (US)

( * ) Notice: Subject to any disclaimer, the term of this patent is extended or adjusted under 35 U.S.C. 154(b) by 200 days.

(21) Appl. No.: 10/065,504

(22) Filed: Oct. 25, 2002

(65) Prior Publication Data

US 2004/0083217 A1 Apr. 29, 2004

(51) Int. Cl.[7] .............................................. G06F 17/30
(52) U.S. Cl. ........................... 707/104.1; 707/6; 707/7; 707/102
(58) Field of Search ............................... 707/6, 7, 102, 707/104.1; 705/3, 2, 4

(56) References Cited

U.S. PATENT DOCUMENTS 6,542,902 B2 * 4/2003 Dulong et al. ............ 707/104.1

| 6,694,334 B2 | * | 2/2004 | DuLong et al. | 707/104.1 |
| 2001/0049673 A1 | * | 12/2001 | Dulong et al. | 707/1 |
| 2003/0120458 A1 | * | 6/2003 | Rao et al. | 702/181 |
| 2003/0125985 A1 | * | 7/2003 | Rao et al. | 705/2 |
| 2003/0130871 A1 | * | 7/2003 | Rao et al. | 705/2 |
| 2003/0172081 A1 | * | 9/2003 | Dulong et al. | 707/100 |
| 2003/0208379 A1 | * | 11/2003 | Haskey et al. | 705/2 |

FOREIGN PATENT DOCUMENTS

| WO | WO 2003040878 A2 | * | 5/2003 | G06F/00/00 |
| WO | WO 2003040990 A2 | * | 5/2003 | G06F/17/60 |

* cited by examiner

Primary Examiner—Frantz Coby
(74) Attorney, Agent, or Firm—Cantor Colburn LLP

(57) ABSTRACT

A method for collecting and distributing clinical data for data mining. The method comprises selecting a local report for collection, where the local report is a structured reporting object and includes a local clinical code, patient identification data and report collections status data. The local report is sanitized by removing the patient identification data. The local report collection status is updated to reflect the selecting. The local report is mapped to a common format report and the mapping includes: accessing a knowledge base that includes the local clinical code and a corresponding common format clinical code; and replacing the local clinical code with the corresponding common format code. The common format report is then transmitted to a data mining host system that includes a data repository.

25 Claims, 3 Drawing Sheets

METHOD, SYSTEM, AND COMPUTER PRODUCT FOR COLLECTING AND DISTRIBUTING CLINICAL DATA FOR DATA MINING

BACKGROUND OF INVENTION

The present disclosure relates generally to a method for collecting and distributing clinical data for data mining and in particular, to a method for collecting and distributing coded clinical data that has been created in different hospitals using different clinical data codes and formats.

Hospitals typically utilize computer systems to manage the various departments within the hospital. Data about each patient is collected by a variety of computer systems. For example, a patient may be admitted to the hospital for a Transthoracic Echo (TTE). Information about the patient (e.g., demographics and insurance) could be obtained by the hospital information system (HIS) and stored on a patient record. This information could then be passed to the cardiology department system (commonly known as the cardio vascular information system, or CVIS). Typically the CVIS is a product of one company, while the HIS is the product of another company. As a result, the database between the two will be different. Further, they will capture/retain and send different levels of granularity in the data. Once the patient information has been received by the CVIS, the patient can be scheduled for a TTE in the echo lab. Next, the TTE is performed by the sonographer. Images and measurements are taken and sent to the CVIS server. The reading physician (e.g., an echocardiographer) sits down at a review station and pulls the patient's TTE study. The echocardiographer then begins to review the images and measurements and creates a complete medical report on the study. The medical report can then be coded as a structured report (SR) document including clinical data codes describing the contents of the report. When the echocardiographer completes the medical report, the report is sent to the CVIS server where it is stored and associated with the patient through patient identification data. This completed medical report with clinical data codes is an example of the kind of report that could be sent to a data repository for data mining.

The ability to create a medical record data repository containing medical data from more than one hospital for use in data mining faces several challenges. First, it is difficult to get consistent clinical data that can be compared across hospitals and within hospitals. For example, Doctor W may abbreviate; Doctor X may standardize his reports to capture only a particular set of information that he is interested in; Doctor Y may inflate his reports to includes massive amounts of data that may irrelevant to the given procedure; and Doctor Z may use software that only reports on some information that is searchable, while the rest of his report is unsearchable text. Another challenge affecting the ability to perform medical data mining has to do with obtaining the clinical data in a consistent fashion. For example, Hospital A may use software that records some information that is searchable, leaving the rest as unsearchable text; Hospital B my utilize dictation that produces difficult to search data; and Hospital C may use software that records the same information as the software used at Hospital A, but the labeling of the data collected is different such that a user of the data would have to interpret both labels to know what data has been recorded.

A further challenge faced in attempting to create a common medical data repository for use in data mining is the difficulty in collecting the clinical data to be entered into the repository. Some data mining software defines specific, in-depth data to be collected but this can require users to re-enter the same data that has already been reported on. This can be too cumbersome and lengthy for the physician, technician or nurse to use. Even if the users are willing to re-enter some of the data, only a subset of the data can be obtained through this process.

SUMMARY OF INVENTION

One aspect of the invention is a method for collecting and distributing clinical data for data mining. The method comprises selecting a local report for collection, where the local report is a structured reporting (SR) object and includes a local clinical code, patient identification data and report collections status data. The local report is sanitized by removing the patient identification data. The local report collection status is updated to reflect the selecting. The local report is mapped to a common format report and the mapping includes: accessing a knowledge base that includes the local clinical code and a corresponding common format clinical code; and replacing the local clinical code with the corresponding common format code. The common format report is then transmitted to a data mining host system that includes a data repository.

Another aspect of the invention is a method for collecting and distributing clinical data for data mining. The method comprises receiving a common format report at a data mining host system, where the common format report is an SR object and includes clinical coded medical data. The data mining host system includes a data repository. The contents of the common format report are mapped to fields in the data repository using an XML schema. The contents of the common format report are added to the data repository responsive to the mapping.

Another aspect of the invention is a system for collecting and distributing clinical data for data mining. The system comprises a network and a hospital computer system in communication with the network. The hospital computer system includes software to implement a method. The method comprises selecting a local report located on the hospital computer system for collection, where the local report is an SR object and includes a local clinical code, patient identification data and report collections status data. The local report is sanitized by removing the patient identification data. The local report collection status is updated to reflect the selecting. The local report is mapped to a common format report and the mapping includes: accessing a knowledge base located on the hospital computer system that includes the local clinical code and a corresponding common format clinical code; and replacing the local clinical code with the corresponding common format code. The common format report is then transmitted to a data mining host system that includes a data repository over the network.

A further aspect of the invention is a system for collecting and distributing clinical data for data mining. The system comprises a network and a storage device including a data repository. The system also comprises a data mining host system in communication with the network and the storage device. The data mining host system include software to implement a method comprising receiving a common format report via the network at a data repository located on the storage device, where the common format report is an SR object and includes clinical coded medical data. The contents of the common format report are mapped to fields in the data repository using an XML schema. The contents of the common format report are added to the data repository responsive to the mapping.

A further aspect of the invention is a computer program product for collecting and distributing clinical data for data mining. The computer program product comprises a storage medium readable by a processing circuit and storing instructions for execution by the processing circuit for implementing a method. The method comprises selecting a local report for collection, where the local report is an SR object and includes a local clinical code, patient identification data and report collections status data. The local report is sanitized by removing the patient identification data. The local report collection status is updated to reflect the selecting. The local report is mapped to a common format report and the mapping includes: accessing a knowledge base that includes the local clinical code and a corresponding common format clinical code; and replacing the local clinical code with the corresponding common format code. The common format report is then transmitted to a data mining host system that includes a data repository.

Further aspects of the invention are disclosed herein. The above discussed and other features and advantages of the present invention will be appreciated and understood by those skilled in the art from the following detailed description and drawings.

BRIEF DESCRIPTION OF DRAWINGS

Referring to the exemplary drawings wherein like elements are numbered alike in the several Figures.

DETAILED DESCRIPTION

An embodiment of the present invention provides an infrastructure and process for collecting clinical data. Clinical data that has been stored as a structured reporting (SR) object (e.g., DICOM SR, HL-7 and XML) is collected for use in data mining. An embodiment of the present invention utilizes the emerging DICOM SR standard along with other SR standards thereby removing the need for data re-entry. The clinical data that is collected for data mining is already stored in a defined and known format within each hospital. This hospital specific clinical data is then transformed into a common format and stored in a data repository for use in data mining. An embodiment of the present invention also establishes an infrastructure for the, collection of these standard SR objects. As part of this infrastructure the clinical data being sent to the data repository is sanitized so that patient identity can remain anonymous. In addition, the clinical data records, or reports, are collected without duplication and without workflow inhibition. An embodiment of the present invention also establishes an infrastructure for distributing the SR objects, or providing data mining on the SR objects, using a web-based interface for creating user defined searches. In addition, bundles of sanitized medical reports can be provided to companies to do their own data mining research.

Figure 1:
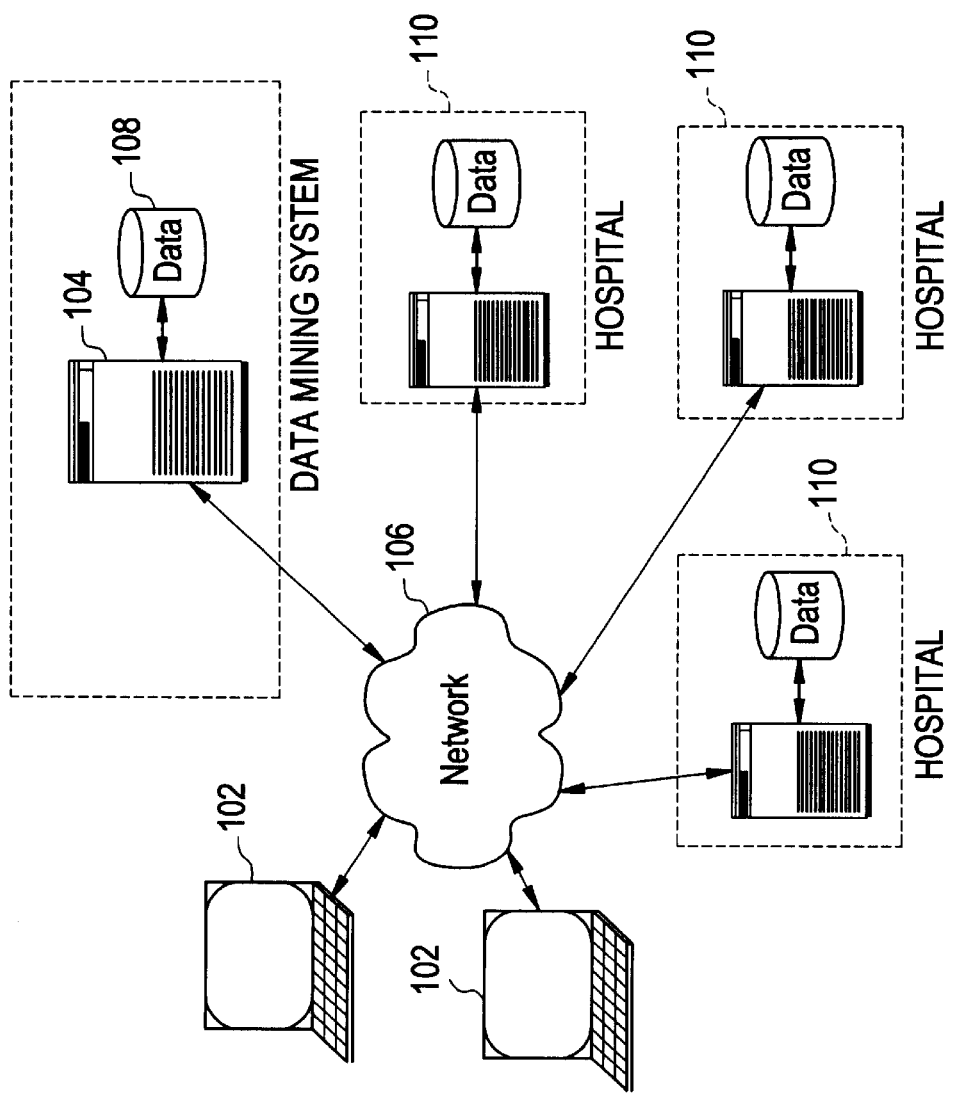
FIG. 1 is an exemplary system for collecting and distributing clinical data for data mining.
Figure 2:
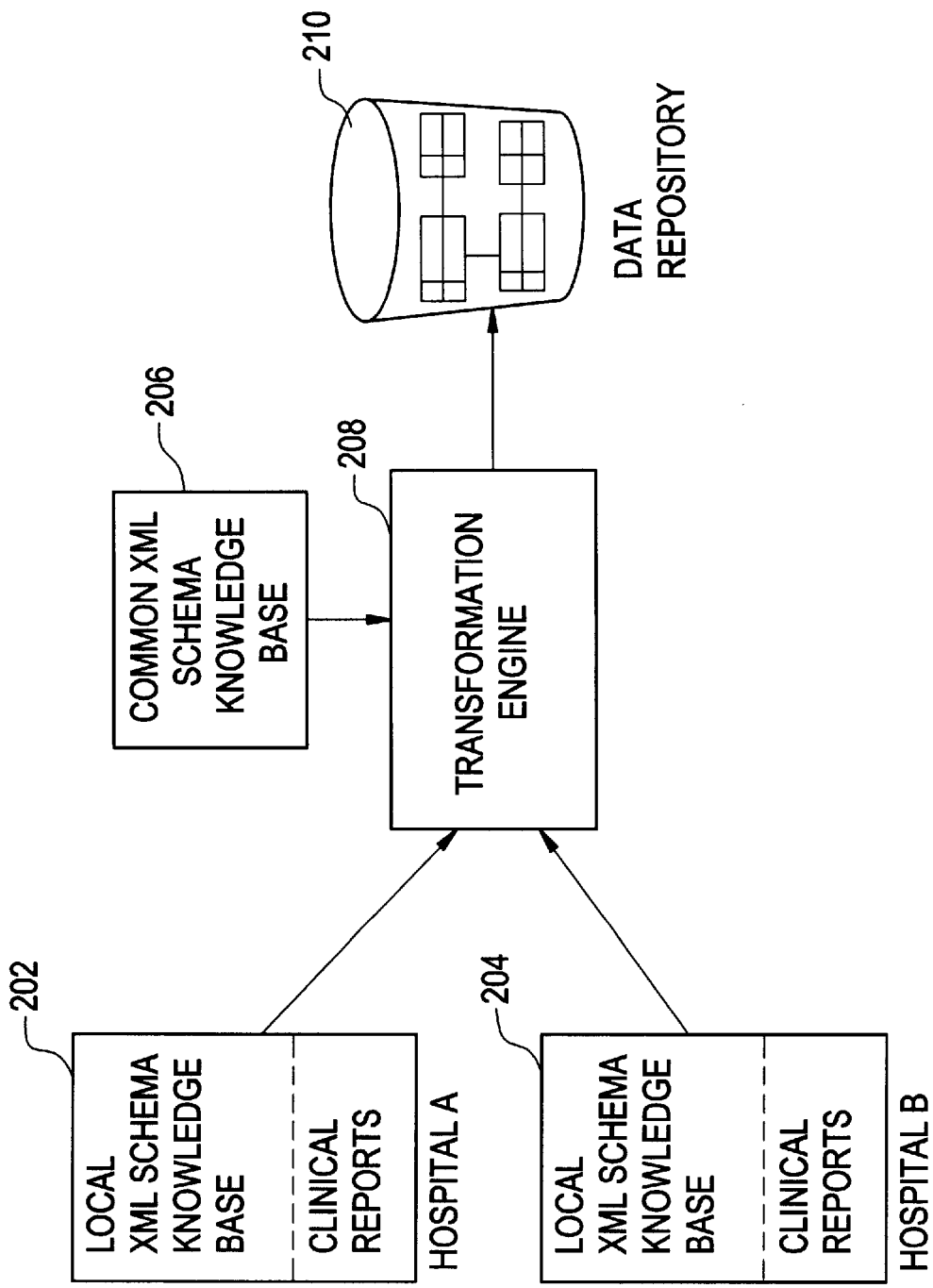
FIG. 2 depicts an exemplary transformation of the clinical reports into a common format for the data repository.

FIG. 1 is an exemplary system for collecting and distributing clinical data for data mining. Hospital computer systems 110 located at various hospitals are connected to a network 106. The hospital computer systems 110 send medical data to a data repository located on a storage device 108 connected to the data mining host system 104. The hospital computer systems 110 typically include application software to perform coded clinical reporting along with one or more storage device for storing the coded clinical reporting data as SR objects. In addition, the hospital computer systems include application software to transform the clinical reporting data stored as SR objects from the hospital format into the common format. The SR objects in the common format are then deposited in the data repository on the storage device 108 for use in data mining. FIG. 2, described below, depicts an exemplary transformation of the clinical reports into a common format for the data repository.

The system of FIG. 1 includes one or more users system 102 through which an end-user, or customer, can make a request to an application program on the data mining host system 104 to access particular records stored in the data repository located on the storage device 108. In an exemplary embodiment, customers can include research hospital staff members, pharmaceutical company research team members and personnel from companies that make medical products. In an exemplary embodiment, the data mining host system 104 executes programs that provide access to data contained in the data repository located on the storage device 108. The user systems 102 can be directly connected to the data mining host system 104 or they could be coupled to the data mining host system 104 via the network, 106. Each user system 102 may be implemented using a general-purpose computer executing a computer program for carrying out the processes described herein. The user systems 102 may be personal computers or host attached terminals. If the user systems 102 are personal computers, the processing described herein may be shared by a user system 102 and the data mining host system 104 by providing an applet to the user system 102.

The network 106 may be any type of known network including a local area network (LAN), a wide area network (WAN), an intranet, or a global network (e.g., Internet). A user system 102 may be coupled to the data mining host system 104 through multiple networks (e.g., intranet and Internet) so that not all user systems 102 are required to be coupled to the data mining host system 104 through the same network. One or more of the user systems 102 and the data mining host system 104 may be connected to the network 106 in a wireless fashion and the network 106 may be a wireless network. In an exemplary embodiment, the network 106 is the Internet and each user system 102 executes a user interface application to directly connect to the data mining host system 104. In another embodiment, a user system 102 may execute a web browser to contact the data mining host system 104 through the network 106. Alternatively, a user system 102 may be implemented using a device programmed primarily for accessing the network 106 such as WebTV.

The data mining host system 104 may be implemented using a server operating in response to a computer program stored in a storage medium accessible by the server. The data mining host system 104 may operate as a network server (often referred to as a web server) to communicate with the user systems 102. The data mining host system 104 handles sending and receiving information to and from user systems 102 and hospital computer systems 110 and can perform associated tasks. The data mining host system 104 may also include a firewall to prevent unauthorized access to the data mining host system 104 and enforce any limitations on authorized access. For instance, an administrator may have access to the entire system and have authority to modify portions of the system and a customer may only have access to view a subset of the data repository records for particular products. In an exemplary embodiment, the administrator has the ability to add new users, delete users and edit user privileges. The firewall may be implemented using conventional hardware and/or software as is known in the art.

The data mining host system 104 also operates as an application server. The data mining host system 104 executes one or more application programs to provide access to the data repository located on a storage device 108, as well as application programs to receive SR objects and to build a data repository for data mining. Processing may be shared by the user system 102 and the data mining host system 104 by providing an application (e.g., java applet) to the user system 102. Alternatively, the user system 102 can include a stand-alone software application for performing a portion of the processing described herein. Similarly, processing may be shared by the hospital computer system 110 and the data mining host system 104 by providing an application to the hospital computer system 110 and alternatively, the hospital computer system 110 can include a stand-alone software application for performing a portion of the processing described herein. It is understood that separate servers may be used to implement the network server functions and the application server functions. Alternatively, the network server, firewall and the application server can be implemented by a single server executing computer programs to perform the requisite functions.

The storage device 108 may be implemented using a variety of devices for storing electronic information such as a file transfer protocol (FTP) server. It is understood that the storage device 108 may be implemented using memory contained in the data mining host system 104 or it may be a separate physical device. The storage device 108 contains a variety of information including a data repository containing medical reports from one or more hospitals in a common format (e.g., using the same clinical codes) and a schema describing the common format and database layout. The data mining host system 104 may also operate as a database server and coordinate access to application data including data stored on the storage device 108. The data repository can be physically stored as a single database with access restricted based on user characteristics or it can be physically stored in a variety of databases including portions of the database on the user systems 102 or the data mining host system 104. In an exemplary embodiment, the data repository is implemented using a relational database system and the database system provides different views of the data to different customers based on customer characteristics.

In an exemplary embodiment of the present invention, clinical data coded using different knowledge bases is transformed to a common/canonical representation.

Hospitals and clinicians use tools for generating clinical reports that depict an outcome of a visit by a patient. These tools use clinical codes to represent, clinical terminology and the clinical codes can differ from one tool to another and from one hospital to another. In addition, the type of SR object used to store the clinical data may differ from one tool to another and from one hospital to another. An exemplary embodiment of the present invention can be utilized to map the clinical reports into a common representation (e.g., common clinical codes and type of SR object). This can provide the ability to query or mine data generated by different clinics and hospitals in a consistent manner and discern patterns that are useful to customers such as researchers and clinicians.

FIG. 2 depicts an exemplary transformation of clinical reports stored as SR objects using hospital specific clinical codes into a common format for the data repository. First, in order to map hospital reports to a common representation, the codes for the clinical terms are categorized and defined. An XML schema can be utilized to define the codes and the format. The clinical codes and categories can either be generated internally or can be based on standards (e.g., SNOMED). Hospital database 202 in FIG. 2 includes data that is stored on a hospital computer system 110 for Hospital A. It includes a local XML schema knowledge base that is utilized to map the local clinical codes and local formats used at Hospital A into a common report format used by the data repository 210. For example, Hospital A may use the code "743.18" to represent a transthoracic echo procedure and the common XML schema knowledge base may use the code "600" to represent a transthoracic echo procedure. Part of the transformation into the common format report would be replacing the local code "743.18" used at Hospital A with the common code "600" utilized by the data repository. Similarly, hospital database 202 includes a local XML schema knowledge base for Hospital B and a clinical report for Hospital B that will be transformed into a common format report with common clinical data codes. Common database 206 located on the data mining host system 104 includes a common XML schema knowledge base for use by the transformation engine 208. In addition, the common database 206 is utilized to create the local XML schema knowledge bases for individual hospitals because it contains a superset of all clinical codes. Along with clinical code translations and SR object translations, the common XML schema knowledge base also includes data repository layout information that determines how the common format reports are represented in the data repository 210.

As shown in FIG. 2, the local clinical report from Hospital A in hospital database 202 is mapped to the common format report, as defined by the common XML schema knowledge base located on the common database 206 by utilizing a transformation engine 208 such as the Extensible Style Language Transformation (XSLT) tool. XSLT is a programming language that can be used to specify transformation rules from one XML document to another XML document. These transformations are specific to the knowledge base used in generating a clinical report. XSLT is the language used in XSL style sheets to transform XML documents into other XML documents. In an exemplary embodiment of the present invention, an XSL processor reads the XML document and follows the instructions in the XSL style sheet and then it outputs a new XML document or XML document fragment. Therefore, as shown in FIG. 2, there would be one set of mapping rules, or local XML schema knowledge base, for every local knowledge base. These rules can be built by the vendor who is supplying the knowledge base for the report generator or by anyone who understands the underlying knowledge base.

The replacement of the local clinical codes with the common clinical codes in order to create a common format report is performed by software located at the hospital computer systems 110 using the local schema knowledge base contained in the hospital database 202. The resulting common format report, containing common clinical codes is then transmitted to the data mining host system 104 to be input to the transformation engine 208 along with the associated local XML schema database located on the hospital database 202 and the common XML schema knowledge base located on the common database 206. The output from the transformation engine 208 is the common format report formatted for the data repository located on the storage device 108. In an alternate exemplary embodiment, all or portions of the transformation engine 208 functions and associated input is located on the hospital computer system 110 and the common format report formatted for the data repository is transmitted to the data mining host system 104 for input to the data repository 210. A single hospital can have more than one local XML schema knowledge base if it utilizes different systems with different formats for clinical reporting. The mapping rules do not need to be expressed as XML schema knowledge bases but could be described in any manner known in the art.

Figure 3:
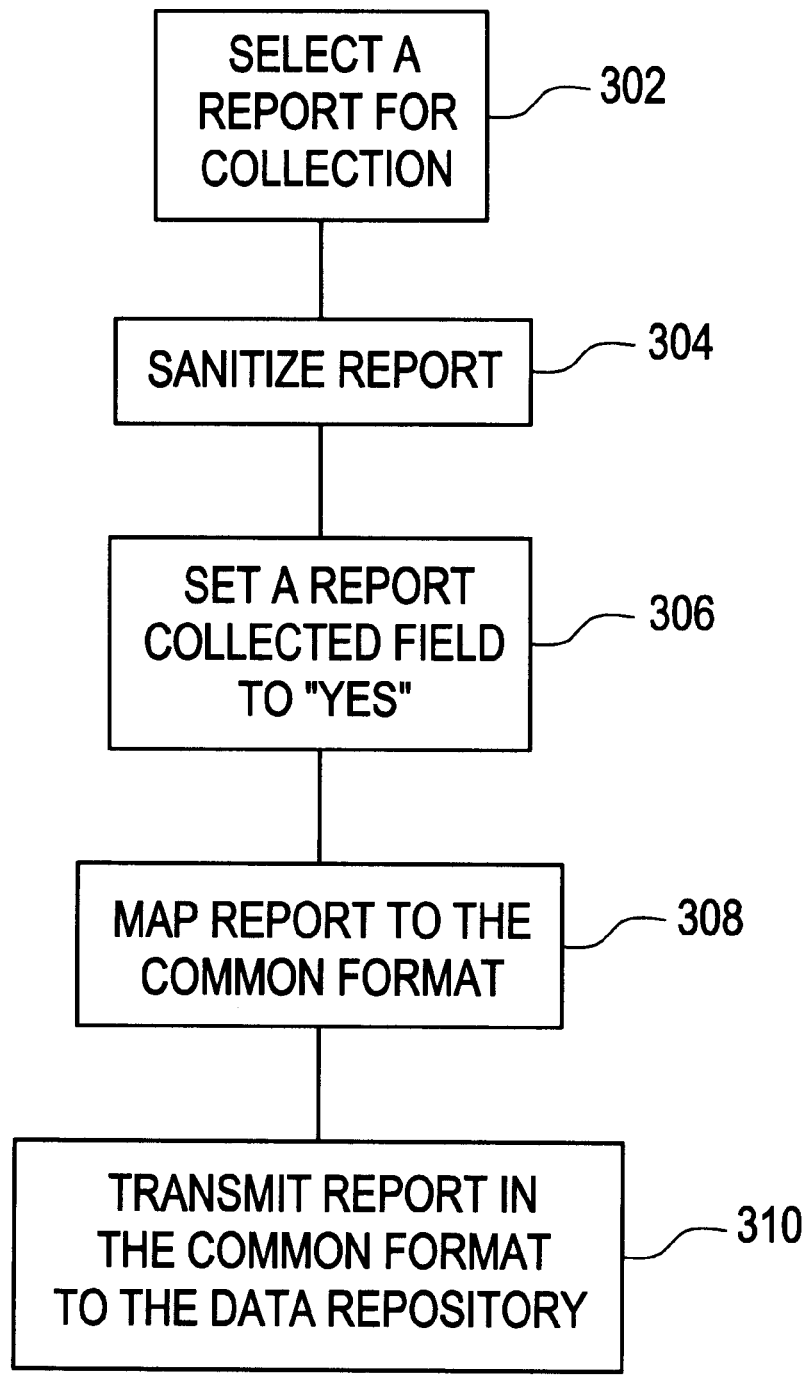
FIG. 3 is an exemplary process for collecting and formatting a report for use in public mining.

FIG. 3 is an exemplary process for collecting and formatting a report for use in public mining. The process would typically occur at the hospitals on the hospital computer systems 110 with the output being sent to the data mining host system 104. At step 302, a report stored on the hospital computer system 110 is selected to be sent to the data repository. The report includes a report collected field that will contain the value "no" if the report has not previously been sent and the value "yes" if it has been sent. This avoids the problem of duplicate reports in the data repository because only reports that contain the value "no" in the report collected field will be sent to the data repository. At step 304, the report is sanitized to remove any data items that could be used to track the medical report back to a particular patient. Removing the data items can include one or both of: replacing the removed data item with an alias for use in grouping reports relating to the same patient; and removing the data item and leaving the data item blank. At step 306, the report collected field is set to "yes" to avoid sending this report to the data repository more than once. Then, at step 308, the report is mapped to the common format, as described in reference to FIG. 2. At step 310, the report that has been mapped into a common format is sent to the data repository for use in data mining. This process of collecting can be performed by off-line administrative transport via regular web based submissions or physical postal service to avoid interfering with workflow.

An embodiment of the present invention allows for clinical data reports that have been created using different coding schemes and different formats to be collected for use in data mining. The reports from each hospital are transformed from a local format into a common format that can be entered into a common data repository for use in data mining. This can be accomplished without requiring any data re-entry by relying on the emerging DICOM SR standard along with the other SR standards that the hospitals utilize to store clinical data. The ability to query a consolidated data repository for clinical data reports can lead to better patient care and more information for medical device and pharmaceutical companies. For example, a stent developing company could use the data to find hidden design problems with their stents and they could use the data to create new stent designs. A pharmaceutical company could use the data repository to make correlations between their medications and procedures performed. In addition, medical researches could use the data to make better procedures for handling complex medical problems and insurance companies could get more detailed clinical information faster to determine better coverage offerings.

As described above, the embodiments of the invention may be embodied in the form of computer-implemented processes and apparatuses for practicing those processes. Embodiments of the invention may also be embodied in the form of computer program code containing instructions embodied in tangible media, such as floppy diskettes, CD-ROMs, hard drives, or any other computer-readable storage medium, wherein, when the computer program code is loaded into and executed by a computer, the computer becomes an apparatus for practicing the invention. An embodiment of the present invention can also be embodied in the form of computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments configure the microprocessor to create specific logic circuits.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Moreover, the use of the terms first, second, etc. do not denote any order or importance, but rather the terms first, second, etc. are used to distinguish one element from another.

What is claimed is:

1. A method for collecting and distributing clinical data for data mining, the method comprising:

selecting a local report for collection, wherein said local report is a structured reporting object and includes a local clinical code, patient identification data and report collection status;

sanitizing said local report by removing said patient identification data;

updating said report collection status to reflect said selecting;

mapping said local report to a common format report, wherein said mapping includes:

accessing a knowledge base that includes said local clinical code and a corresponding common format clinical code; and replacing said local clinical code with said corresponding common format clinical code; and transmitting said common format report to a data mining host system, wherein said data mining host system includes a data repository.

2. The method of claim 1 further comprising:

receiving said common format report at said data mining host system;

mapping the contents of said common format report to fields in said data repository; and adding the contents of said common format report to said data repository responsive to said mapping the contents of said common format report.

3. The method of claim 1 further comprising:

receiving a request from a customer to access data contained in said data repository, wherein said request includes a data query;

verifying that said customer has access to said data; and transmitting said data to said customer in response to said verifying.

4. The method of claim 1 wherein said customer is a research hospital staff member.

5. The method of claim 1 wherein said customer is a pharmaceutical company research team member.

6. The method of claim 1 wherein said customer is from a corporation that makes medical devices.

7. The method of claim 1 wherein said structured reporting object is an XML object.

8. The method of claim 1 wherein said structured reporting object is a DICOM structured reporting object.

9. The method of claim 1 wherein said structured reporting object is an HL-7 message object.

10. A method for collecting and distributing clinical data for data mining, the method comprising:

receiving a common format report at a data mining host system, wherein said data mining host system includes a data repository and wherein said common format report is a structured reporting object including clinical coded medical data;

mapping the contents of said common format report to fields in said data repository using an XML schema; and adding the contents of said common format report to said data repository responsive to said mapping.

11. The method of claim 10 further comprising:

receiving a request from a customer to access data contained in said data repository, wherein said request includes a data query;

verifying that said customer has access to said data; and transmitting said data to said customer in response to said verifying.

12. The method of claim 11 wherein said customer is a research hospital staff member.

13. The method of claim 11 wherein said customer is a pharmaceutical company research team member.

14. The method of claim 11 wherein said customer is from a corporation that makes medical devices.

15. The method of claim 10 wherein said structured reporting object is an XML object.

16. The method of claim 10 wherein said structured reporting object is a DICOM structured reporting object.

17. The method of claim 10 wherein said structured reporting object is an HL-7 message object.

18. A system for collecting and distributing clinical data for data mining, the system comprising:

a network; and a hospital computer system in communication with said network, said hospital computer system including software to implement the method comprising:

selecting a local report located on said hospital computer system for collection, wherein said local report is a structured reporting object and includes a local clinical code, patient identification data and report collection status;

sanitizing said local report by removing said patient identification data;

updating said report collection status to reflect said selecting;

mapping said local report to a common format report, wherein said mapping includes:

accessing a knowledge base located on said hospital computer system that includes said local clinical code and a corresponding common format clinical code; and replacing said local clinical code with said corresponding common format clinical code; and transmitting said common format report over said network to a data mining host system, wherein said data mining host system includes a data repository.

19. The system of claim 18 wherein said network is an Internet.

20. The system of claim 18 wherein said network is an intranet.

21. A system for collecting and distributing clinical data for data mining, the system comprising:

a network;

a storage device including a data repository; and a data mining host system in communication with said network and said storage device, said data mining host system including software to implement the method comprising:

receiving a common format report via said network at said data mining host system, wherein said common format report is a structured reporting object including clinical coded medical data;

mapping the contents of said common format report to fields in said data repository using an XML schema; and adding the contents of said common format report to said data repository responsive to said mapping.

22. The system of claim 21 wherein said network is an Internet.

23. The system of claim 21 wherein said network is an intranet.

24. The system of claim 21 wherein data repository is a relational database.

25. A computer program product for collecting and distributing clinical data for data mining, the product comprising:

a storage medium readable by a processing circuit and storing instructions for execution by the processing circuit for:

selecting a local report located on said hospital computer system for collection, wherein said local report is a structured reporting object and includes a local clinical code, patient identification data and report collection status;

sanitizing said local report by removing said patient identification data;

updating said report collection status to reflect said selecting;

mapping said local report to a common format report, wherein said mapping includes:

accessing a knowledge base that includes said local clinical code and a corresponding common format clinical code; and replacing said local clinical code with said corresponding common format clinical code; and transmitting said common format report to a data mining host system, wherein said data mining host system includes a data repository.

* * * * *